United States Patent [19]

McPhee

[11] Patent Number: 5,654,441

[45] Date of Patent: Aug. 5, 1997

[54] SYNTHESIS OF 1,3-OXATHIOLANE SULFOXIDE COMPOUNDS

[75] Inventor: Derek James McPhee, Guelph, Canada

[73] Assignee: Uniroyal Chemical Ltd./Ltee, Elmira, Canada

[21] Appl. No.: 528,451

[22] Filed: Sep. 14, 1995

[51] Int. Cl.[6] .................... C07D 327/06; C07D 327/04
[52] U.S. Cl. .................. 549/14; 549/40; 549/30
[58] Field of Search .................. 549/40, 14, 30

[56] References Cited

U.S. PATENT DOCUMENTS

| | | | |
|---|---|---|---|
| 3,249,499 | 5/1966 | Schmeling | 167/33 |
| 3,393,202 | 7/1968 | Kulka | 260/327 |
| 4,115,440 | 9/1978 | Sheng et al. | 562/533 |
| 4,152,334 | 5/1979 | Lee | 549/14 |
| 4,182,716 | 1/1980 | Znotins et al. | 549/14 |
| 4,247,707 | 1/1981 | Znotins | 549/22 |

OTHER PUBLICATIONS

Lee et al, "Synthesis of Dihydro–1,4–oxathiins by Rearrangement of 1,3–Oxathiolane Sulfoxides", J. Org. Chem. 51:2789–2795 (1986).

Reich et al, "Seleninic Acids as Catalysts for Oxidations of Olefins and Sulfides Using Hydrogen Peroxide", Synthesis, Apr. 1978, pp. 299–301.

Lee et al, "Sulfenic Acid derived from 1,3–oxathiolane–3–oxide", Taehan Hwahakhoe Chi 31(2): 197–202 (1987) (English language translation).

Lee et al, "Sulfene Acid derived from 1,3–oxathnolane–3–oxide", Chem. Abs. vol. 108. No. 5888d. (1988).

*Primary Examiner*—Jose' G. Dees
*Assistant Examiner*—Deborah Lambkin
*Attorney, Agent, or Firm*—Daniel Reitenbach

[57] ABSTRACT

A process for the production of a 1,3-oxathiolane sulfoxide of the formula

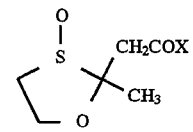

(I)

wherein X is an amino group of the formula —NHR, wherein R is hydrogen, phenyl, $C_1$–$C_8$ alkyl, $C_3$–$C_6$ cycloalkyl, nitrophenyl, ($C_1$–$C_4$ alkoxy)phenyl, furfuryl, halophenyl, tolyl, napthyl, biphenyl or hydroxyphenyl; or X is an alkoxy group of the formula —$OR^1$ wherein R is $C_1$–$C_6$ alkyl, which process comprises oxidizing a 1,3-oxathiolane of the formula

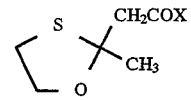

(IA)

wherein X is as defined above, in the presence of an effective amount of aqueous hydrogen peroxide and a sterically-hindered organoselenium compound of the formula

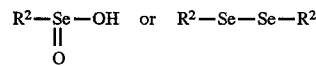

wherein $R^2$ is aryl, mono-, di- or tri-substituted with $C_1$–$C_3$ alkyl, to the produce the 1,3-oxathiolane sulfoxide. This process stereoselectively produces the cis stereoisomer of the 1,3-oxathiolane sulfoxide. Additionally, there is disclosed a novel method for the preparation of 5,6-dihydro-2-methyl-1,4-oxathiin compounds using this process.

22 Claims, No Drawings

SYNTHESIS OF 1,3-OXATHIOLANE SULFOXIDE COMPOUNDS

FIELD OF THE INVENTION

The present invention relates to an improved process for producing 1,3-oxathiolane sulfoxide compounds. More particularly, the present invention relates to an improved process for the stereoselective synthesis of the cis-stereoisomer of certain 1,3-oxathiolane sulfoxide compounds. This invention also relates to an improved process for the production of 5,6-dihydro-2-methyl-1,4-oxathiin compounds.

BACKGROUND OF THE INVENTION

Stereoisomers are molecules which possess identical chemical formulas with the same atoms bonded to one another, but differ in the manner in which these atoms are arranged in three-dimensional space. While the structural differences between stereoisomers are subtle and of little consequence in some chemical reactions, they can be very important in compounds utilized in biological systems, such as agricultural chemicals, drugs and other biologically active compounds, and in intermediates used to prepare these compounds.

Synthesis of these biologically-active compounds by techniques which produce racemic intermediate mixtures frequently result in compounds with lower specific bioactivity due to the presence of undesired stereoisomers which are biologically or functionally inactive.

A chemical reaction is said to be stereoselective if one set of stereoisomers is formed exclusively or predominantly. It can be commercially important to stereoselectively synthesize the desired isomer of an intermediate in the production of some biologically active compounds. The use of stereoselective reactions in the manufacture of such biologically-active compounds can also help minimize waste and disposal problems associated with the production of unwanted isomeric byproducts.

U.S. Pat. Nos. 3,249,499 and 3,393,202 describe the preparation of certain 5,6-dihydro-1,4-oxathiin compounds without the use of an intermediate 1,3-oxathiolane sulfoxide. The preparation methods described therein involve the use of chlorinating agents.

In an alternative method for the production of 5,6-dihydro-1,4-oxathiin compounds, one of the intermediates is a 1,3 oxathiolane sulfoxide which is stereospecific, i.e., it can exist in a "cis" or "trans" configuration. It is known to those skilled in the art that the cis stereoisomers of certain 1,3 oxathiolane sulfoxides lead to a higher yields of the desired oxathiin product. Both of the "cis" and "trans" sulfoxide stereoisomers are products of the oxidation of 1,3-oxathiolane. See, for example, Lee et al., J. Org. Chem. 51, 2789–2795 (1986).

A method of synthesis of 5,6-dihydro-1,4-oxathiin compounds which utilizes a 1,3-oxathiolane sulfoxide as an intermediate, is described in U.S. Pat. Nos. 4,152,334; 4,182,716; and 4,247,707, which essentially consists of oxidizing a 1,3-oxathiolane in the presence of hydrogen peroxide to produce a 1,3-oxathiolane sulfoxide intermediate as a mixture of the two possible stereoisomers, and then subjecting the 1,3-oxathiolane sulfoxide intermediate to acid-catalyzed rearrangement to form the desired oxathiin carboxanilide.

In the rearrangement of mixtures of the cis and trans isomers of 1,3-oxathiolane sulfoxide intermediate, unwanted byproducts are formed in amounts proportional to the amount of trans stereoisomer present in the mixture. It would be desirable, therefore, to maximize the yield of the cis stereoisomer of the 1,3-oxathiolane sulfoxide intermediate and minimize the yield of trans stereoisomer, during the oxidation step.

Methods for stereoselective synthesis of 1,3-oxathiolane sulfoxides have been previously described. Lee et al, supra, report that oxidation of 2-methyl-N-phenyl-1,3-oxathiolane-2-acetamide with hydrogen peroxide in acetic acid produces a 70:30 mixture of the cis stereoisomer to the trans stereoisomer, whereas similar oxidation with 85% m-chloroperbenzoic acid produces an 85:15 cis: trans mixture.

Lee and Park, Taehan Hwahakhoe Chi 31, 197–202 (1987); Chemical Abstracts 108, 5888d (1988) describe the use of a combination of aqueous hydrogen peroxide and benzeneseleninic acid at –5° to 0° C. to prepare a mixture of sulfoxides with a cis:tran stereoisomer ratio of 93:7.

However, the procedure in Lee and Park supra, is not suitable for commercial production. Quantitative overoxidation of the sulfoxides to give sulfones resulting from the the presence of excess aqueous hydrogen peroxide and benzeneseleninic acid, can be a major undesirable side reaction. See, for example, Reich et al., Synthesis, 299–301 (1978). Overoxidation can only be avoided by carefully controlling the activity of the oxidant in the reaction, requiring either very low temperatures and/or very slow addition rates of the oxidant to moderate the rate of reaction and avoid the presence of excess oxidant at any given time. Such low temperatures and very slow rates of addition are cumbersome to achieve and maintain, and are, therefore, not amenable to large-scale production.

It is an object of this invention to provide a new method for the preparation of 1,3-oxathiolane sulfoxide compounds. In particular, it is an object of this invention to provide a novel process for the stereoselective preparation of the cis-stereoisomer of 1,3-oxathiolane sulfoxide compounds which is commercially useful. It is a further object to provide a novel process for the preparation of 5,6-dihydro-1,4-oxathiin compounds.

SUMMARY OF THE INVENTION

The present invention relates to a process (Process I) for the production of a 1,3-oxathiolane sulfoxide of the formula

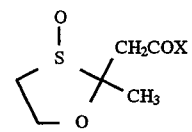
(I)

wherein X is an amino group of the formula —NHR, wherein R is hydrogen, phenyl, $C_1$–$C_8$ alkyl, $C_3$–$C_6$ cycloalkyl, nitrophenyl, ($C_1$–$C_4$ alkoxy)phenyl, furfuryl, halophenyl, tolyl, napthyl, biphenyl or hydroxyphenyl; or X is an alkoxy group of the formula —$OR^1$ wherein R is $C_1$–$C_6$ alkyl, which process comprises oxidizing a 1,3-oxathiolane of the formula

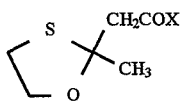
(IA)

wherein X is as defined above, in the presence of an effective mount of aqueous hydrogen peroxide and a sterically-hindered organoselenium compound of the formula

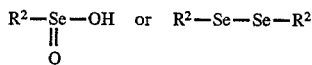

wherein $R^2$ is aryl, mono-, di- or tri-substituted with $C_1$-$C_3$ alkyl, to produce the 1,3-oxathiolane sulfoxide.

The present invention a/so relates to a process (Process II) for the production of a 5,6-dihydro-2-methyl-1,4-oxathiin compound of the formula

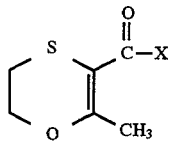

(II)

wherein X is as defined above, which process comprises (a) oxidizing a 1,3-oxathiolane of the formula

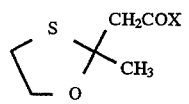

(IA)

wherein X is as defined above, in the presence of an effective amount of aqueous hydrogen peroxide and a sterically-hindered organoselenium compound of the formula

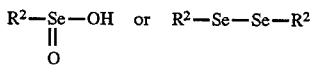

wherein $R^2$ is as defined above, to the produce a 1,3-oxathiolane sulfoxide of the formula

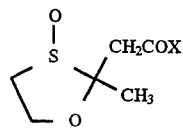

(I)

wherein X is as defined above; and (b) combining the 1,3-oxathiolane sulfoxide with a nonprotic organic solvent to form a reaction mixture; and heating the reaction mixture at a temperature of about 30° C. to about 100° C., in the presence of an effective amount of an acid catalyst with a $pK_a$ of about 0.5 to about 4.5, while removing the water of reaction, to produce the 5,6-dihydro-2-methyl-1,4-oxathiin compound.

DESCRIPTION OF THE INVENTION

The 1,3-oxathiolane of Formula IA can be prepared by procedures known in the art, such as, for example, by reacting an acetoacetamide or an alkyl acetoacetate with 2-mercaptoethanol. See, e.g., U.S. Pat. No. 4,152,334.

For purposes of this invention, the "cis" and "trans" stereoisomers of the 1,3-oxathiolane sulfoxide compound of Formula I, refer to the relative configurations of the sulfoxide S—O bond and the $CH_2$—CO—X side chain in the compound, as depicted below:

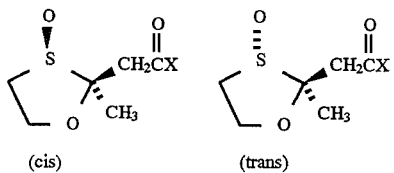

The cis stereoisomer is preferred.

Process I of the present invention and step (a) of Process II of the present invention, preferably produce the cis stereoisomer of the 1,3-oxathiolane sulfoxide of Formula I substantially free of the trans stereoisomer of the 1,3-oxathiolane sulfoxide. For the purposes of this invention, the 1,3-oxathiolane sulfoxide is substantially free of the trans stereoisomer of the 1,3-oxathiolane sulfoxide if the ratio of the cis stereoisomer of the 1,3-oxathiolane sulfoxide to the trans stereoisomer of the 1,3-oxathiolane (cis:trans ratio) is at least 95:5 (w/w), preferably at least 97:3 (w/w), and most preferably, at least 99:1 (w/w).

In Process I and Process II of this invention, X is preferably an amino group of the formula —NHR, wherein R is phenyl, nitrophenyl, ($C_1$-$C_4$ alkoxy)phenyl, halophenyl or hydroxyphenyl; or X is an alkoxy group of the formula —$OR^1$ wherein R is $C_1$-$C_6$ alkyl. Most preferably, X is an amino group of the formula —NHR, wherein R is phenyl.

Preferable organoselenium compounds useful in Process I and Process II of this invention are the substituted arylseleninic acids of the formula $R^2SeOOH$ described above, wherein the selenium moiety is sterically-hindered by the presence of one or more adjacent alkyl groups, such as 2-alkylbenzeneseleninic acids, 2,6-dialkylbenzeneseleninic acids, or 2,4,6-trialkylbenzeneseleninic acids. For the purposes of this invention, the term "sterically-hindered" means that the "active" portion of the oxidizing agent (the selenium moiety) is made less accessible physically to the sulfur atom of the oxathiolane ring.

If the bisaryl diselenide compounds of the formula $R^2SeSeR^2$ described above, are selected as the organoselenium compound for use in Process I and Process II of this invention, the bisaryl diselenide compound is preferably reacted with the aqueous hydrogen peroxide prior to addition of the 1,3-oxathiolane compound.

The amounts of the organoselenium compound required can be varied between the stoichiometrically equivalent mount, to a catalytic amount of no more than 1% of the number of moles of sulfide to be oxidized, used in combination with a stoichiometric amount of aqueous hydrogen peroxide or a slight excess thereof. Preferably, the amount of aqueous hydrogen peroxide and the organoselenium will be an amount effective to produce the cis stereoisomer of the 1,3-oxathiolane sulfoxide substantially free of the trans stereoisomer of the 1,3-oxathiolane sulfoxide.

The sterically-hindered organoselenium compounds useful in the process of this invention can be either prepared by known methods, or are commercially available. The synthesis of bis-(2,6-dimethylphenyl) diselenide and 2,6-dimethylbenzeneseleninic acid are described in Examples 4 and 5 below.

The sterically-hindered organoselenium compound is preferably the sterically-hindered arylseleninic acid wherein $R^2$ is phenyl, mono-, di- or tri-substituted with $C_1$-$C_3$ alkyl; more preferably, wherein $R^2$ is phenyl, mono-, di- or tri-substituted with methyl; and, most preferably, wherein $R^2$ is phenyl, tri-substituted with methyl. Useful organoselenium compounds in the process of this invention include 2-methylbenzeneseleninic acid, 2,6- dimethylbenzeneseleninic acid, and 2,4,6-trimethylbenzeneseleninic acid.

The oxidation of the 1,3-oxathiolane in Process I and in step (a) of Process II is preferably carried out in an effective two phase mixture of water and a suitable organic solvent. The oxidation is preferably carried out at temperatures ranging from about 0° C. to about 15° C. The oxidation reaction is preferably allowed to proceed until all the starting material has been consumed, as evidenced, e.g., by thin-layer chromatography. After the completion of the oxidation reaction, the desired 1,3-oxathiolane sulfoxide can be easily recovered from the organic phase, while the organoselenium compound can be extracted from the aqueous phase, if so desired, for subsequent reuse. The reaction can be made catalytic in the organoselenium compound since the organoselenium compound can be recovered from the reaction mixture at the end of the oxidation step by a variety of methods known in the art.

A suitable organic solvent useful in the oxidation step of the process of this invention is a nonprotic organic solvent which is immiscible with water. Suitable solvents include, but are not limited to, aromatic hydrocarbons having a boiling point not greater than 145° C., chlorinated hydrocarbons having a boiling point not greater than 130° C., or alkyl esters of aliphatic acids having a boiling point not greater than 130° C. Examples of solvents in these categories include benzene, toluene, and xylene (aromatic); chloroform, dichloromethane; (chlorinated hydrocarbons); ethyl acetate, n-propyl acetate, iso-propyl acetate (alkyl esters). Preferred solvents are chlorinated hydrocarbons. A particularly preferred solvent is dichloromethane.

Process II of this invention proceeds, in part, according to the following reaction scheme:

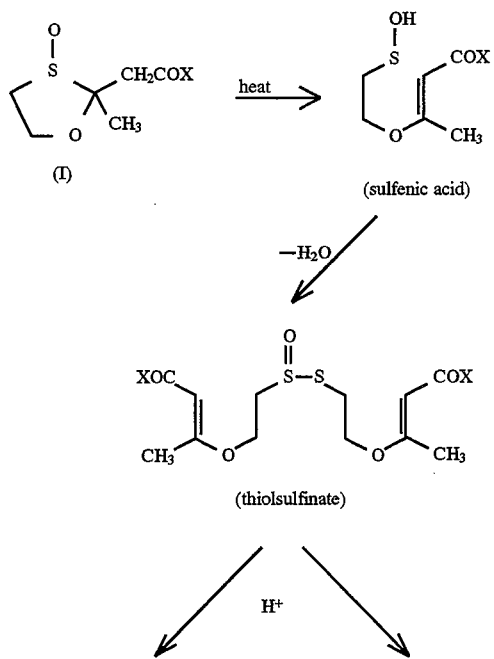

In Process II of this invention, the 1,3-oxathiolane sulfoxide is heated, preferably at a temperature of about 30° C. to about 100° C., and, more preferably, at a temperature of about 50° C. to about 80° C., in a nonprotic organic solvent in the presence of an effective amount of an acid catalyst with a $pK_a$ of, preferably, about 0.5 to about 4.5, and more preferably, about 1.0 to about 3.5, while removing the water of reaction, to produce the pre-II intermediate. The reaction mixture is then neutralized, to produce the 5,6-dihydro-2-methyl-1,4-oxathiin compound of formula II. Suitable nonprotic organic solvents include the nonprotic organic solvents described above as useful in the preparation of the 1,3-oxathiolane sulfoxide of Formula I. Suitable acid catalysts include adipic acid ($pK_a$4.43), bromobenzoic acid ($pK_a$3.81), mandelic acid ($pK_a$3.41), pyridinium p-toluenesulfonate ($pK_a$3.00), methylmalonic aicd ($pK_a$3.07), fumaric acid ($pK_a$3.03), phenylmalonic ($pK_a$2.58), 2-nitrobenzoic acid ($pK_a$2.18), 2-chloro-5-nitrobenzoic acid ($pK_a$2.12), 2-chloro-4-benzoic acid ($pK_a$1.96), maleic acid ($pK_a$1.91), oxalic acid ($pK_a$1.23), and preferably, malonic acid ($pK_a$2.83). An effective amount of the acid catalyst is the amount of the acid catalyst that will result in the splitting of the dimeric thiolsulfinate (see scheme above) to form pre-II, the precursor of the 5,6-dihydro-2-methyl-1,4-oxathiin compound of formula II. This amount can vary but, in general, will be between about 1% and 25%, preferably about 5%, by weight, of the 1,3-oxathiolane sulfoxide present in the reaction mixture.

Any appropriate base can be used to neutralize the reaction mixture, including organic and inorganic bases, such as sodium hydroxide, sodium bicarbonate, sodium acetate, or sodium formate.

The following examples are provided to illustrate the present invention.

EXAMPLES

Chromatographic analyses of the reaction products were carried out on an HPLC system consisting of a Waters 600 Multisolvent Delivery System, a Waters 440 Absorbance Detector operating at 254 nm, a Waters 710B WISP autosampler and a Waters 740 Data Module and equipped with a Waters µ-BONDAPAK C18 column (10µ, 3.9×300 mm). Samples were eluted with a methanol-water gradient.

Example 1

Synthesis of cis-2-methyl-N-phenyl-1,3-oxathiolane-2-acetamide-3-oxide using a seleninic acid catalyst 2-Methyl-N-phenyl-1,3-oxathiolane-2-acetamide (23.7 g, 0.1 moles), o-xylene (91.2 g) and 2,4,6-trimethylphenylseleninic acid (0.5 g, 2.16 mmoles) were placed in a 1 L three-necked round bottom flask equipped with a mechanical stirrer, a condenser and a thermometer, to produce a reaction mixture. The reaction mixture was cooled to 10°–15° C. with the aid of an ice-water bath. Aqueous hydrogen peroxide (9.6 g, 37.5% concentration, approximately 1.05 equivalents) was then added dropwise to the reaction mixture with stirring over a period of 30 minutes.

After the peroxide addition was complete, the resultant reaction mixture was stirred at the same temperature (10°–15° C.) for one hour and then transfered to a separatory funnel and washed with aqueous potassium carbonate solution, producing a three layer system, i.e., a bottom layer, a middle layer and a top layer. The bottom layer, which consisted of essentially pure oily sulfoxide was decanted, followed by the middle aqueous layer. The top o-xylene layer was combined with the bottom sulfoxide layer previously decanted. The aqueous phase was returned to the separatory funnel and extracted twice with dichloromethane.

The dichloromethane extracts were combined and analyzed by HPLC, which indicated the presence of essentially pure cis-2-methyl-N-phenyl-1,3-oxathiolane-2-acetamide-3-oxide. Removal of the dichloromethane produced a quantitative yield of sulfoxide as a straw coloured oil that promptly crystallized on standing. This material had spectroscopic properties identical to those previously reported in the literature for this compound and its 300 MHz N.M.R. spectrum showed no traces of the undesired trans-2-methyl-N-phenyl-1,3-oxathiolane-2-acetamide-3-oxide. The "cis" stereochemistry of the product was confirmed by X-ray analysis of a suitable single crystal isolated from a recrystallized portion of material.

Example 2

Synthesis of cis-2-methyl-N-phenyl-1,3-oxathiolane-2-acetamide-3-oxide using a diselenide catalyst 2.5 g (6.3 mmoles) of bis-(2,4,6-trimethylphenyl) diselenide were placed in a 1 L three-necked round bottom flask equipped with a mechanical stirrer, a condenser and a thermometer. The diselenide was then dissolved with stirring in 15 mL of dry methylene chloride. Aqueous hydrogen peroxide (0.55 equivalents) was then added dropwise and the resulting reaction mixture was stirred for 15 minutes or until the yellow colour of the diselenide had disappeared. The resulting seleninic acid precipitated out as a white solid.

The solvent was removed from the precipitated seleninic acid solid by briefly drawing air through the system with a water aspirator pump. 2-Methyl-N-phenyl-1,3-oxathiolane-2-acetamide (120.2 g, 0.5 moles) dissolved in 450 g of isopropyl acetate were added to the seleninic acid solid in the reactor and the resulting mixture was cooled to 10°–15° C. with the aid of an ice-water bath. Aqueous hydrogen peroxide (48.3 g, 36.8% concentration, approximately 1.05 equivalents) was added dropwise with stirring over a period of 30 minutes. After the peroxide addition was complete, the reaction mixture was stirred at the same temperature for one hour and then transfered to a separatory funnel and washed, first with aqueous potassium carbonate solution and afterwards with aqueous sodium chloride solution.

The organic layer was separated and concentrated on a rotary evaporator (under water aspirator vacuum and with a bath temperature of 30° C.) to produce cis-2-methyl-N-phenyl-1,3-oxathiolane-2-acetamide-3-oxide as a nearly colourless oil which crystallized upon standing. This material had spectroscopic properties identical to those previously reported in the literature for cis-2-methyl-N-phenyl-1,3-oxathiolane-2-acetamide-3-oxide and HPLC analysis showed it to be of a purity of greater than 99.5%.

Example 3

Catalyst Recovery

The seleninic catalyst was recovered from the reaction mixtures described in Examples 1 and 2 above for recycle and reuse using the following procedure:

The combined aqueous washes from the oxidation reactions were cooled to 10°–15° C., acidified to a pH of 3 and then treated with an excess of sodium sulfite, sodium hydrogen sulfite or sodium dithionite. At this point, the seleninic acid precipitated out as the corresponding diselenide (identified by its bright yellow or orange colour).

To maximize the catalyst recovery the aqueous phase was then extracted, after filtering off the precipitated diselenide, with one or more portions of dichloromethane.

The filtered solid and the dichloromethane extracts were combined, dried and concentrated to afford an essentially quantitative recovery of pure diselenide, which can be reused in subsequent sulfide oxidation reactions without any appreciable difference in the yields and/or composition of the sulfoxides formed.

Example 4

Preparation of bis-(2,6-dimethylphenyl) diselenide

A 1 L four-necked round bottom flask equipped with a mechanical stirrer, a condenser connected to a gas bubbler, a pressure equalized solids addition funnel charged with 10.3 g (0.13 moles) of 100 mesh selenium metal powder and a thermometer and containing 2,6-dimethylphenylmagnesium bromide [prepared from 3.7 g (0.15 moles) of magnesium turnings and 25 g (0.135 moles) of 2-bromo-m-xylene in 100 mL of anhydrous tetrahydrofuran (THF)] was purged with nitrogen and kept under a slight positive nitrogen pressure throughout the reaction while the selenium metal was added in small portions at such a rate that the reaction temperature did not exceed 40° C.

After the addition was complete, the resulting greenish suspension was stirred for an additional 30 minutes at room temperature and then 30 minutes at reflux. The reaction mixture was then cooled to room temperature and then poured into a mixture of 50 mL of concentrated HCl and 500 g of crushed ice contained in a 2 L erlenmeyer flask and stirred until all the ice had melted This step was done in an efficient fumehood since the hydrolysis results in the formation of 2,6-dimethylphenylselenol with pungent odor.

The resulting two phase mixture was filtered through a 2 cm pad of Celite® to remove any traces of unreacted selenium metal and the filtrate was extracted four times with 250 mL of methylene chloride. The bright yellow combined organic extracts were concentrated to a volume of about 500 mL, then 200 mL of water containing 5.6 g (0.1 moles) of KOH were added and the two phase system was stirred vigorously with cooling to 0° C. and then treated with 35% aqueous hydrogen peroxide (0.05 moles) and 0.5 g of tetrabutyl ammonium bromide.

After stirring for 30 minutes the organic layer was decanted, dried over anhydrous magnesium sulfate and concentrated to afford the title compound as a bright orange crystalline solid, m.p. 60°–62° C. No further purification was required as this material showed the expected spectroscopic properties and gave an elemental analysis within acceptable limits.

Example 5

Preparation of 2,6-dimethylphenylseleninic acid

This material was prepared by the method described in Example 2. After the addition of 0.55 equivalents of aqueous hydrogen peroxide to a dichloromethane solution of bis(2,6-dimethylphenyl)diselenide and stirring until the solution became colourless, the solution was concentrated to one-half the original volume and cooled until the title compound precipitated out as a fine white powder, which was removed by filtration and dried in a vacuum desiccator. This material had a melting point of 129°–134° C. (with decomposition) and gave satisfactory spectra and elemental analysis.

Example 6

Preparation of 5,6-dihydro-2-methyl-1,4-oxathiin-3-carboxanilide

Cis-2-methyl-N-phenyl-1,3-oxathiolane-2-acetamide-3-oxide, prepared from 0.1 moles of 2-methyl-N-phenyl-1,3-oxathiolane-2-acetamide as prepared in Example 1, was placed with toluene (100 g), tetrabutylammonium bromide (a phase transfer catalyst) (0.32 g, 0.001 g mole) and malonic acid (pK$_a$=2.83, 0.41 g, 0.004 g mole) in a 1 L three-necked round bottom flask equipped with a mechanical stirrer, a thermometer and a Dean-Stark trap for the efficient removal of evolved water of reaction. The reaction mixture so prepared was placed under a vacuum equivalent of 300 mm of Hg and heated at 72°–75° C. for 1 hour. Methanesulfonic acid (0.19 g, 0.002 g mole) was then added to the reaction mixture, the vacuum was increased to 200 mm Hg and heating was continued at 72°–75° C. for an additional hour. The reaction mixture was then cooled to 55°–60° C. and washed successively with 100 mL portions of 5% aqueous sodium hydroxide solution and water. The resulting organic layer was then decanted and concentrated, and after isolation and drying, yielded a total of 17.3 g of 5,6-dihydro-2-methyl-1,4-oxathiin-3-carboxanilide.

What is claimed is:

1. A process for the production of a 1,3-oxathiolane sulfoxide of the formula

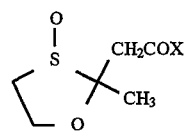

wherein X is an amino group of the formula —NHR, wherein R is hydrogen, phenyl, C$_1$–C$_8$ alkyl, C$_3$–C$_6$ cycloalkyl, nitrophenyl, (C$_1$–C$_4$ alkoxy)phenyl, furfuryl, halophenyl, tolyl, napthyl, biphenyl or hydroxyphenyl; or X is an alkoxy group of the formula —OR$^1$ wherein R' is C$_1$–C$_6$ alkyl, which process comprises oxidizing a 1,3-oxathiolane of the formula

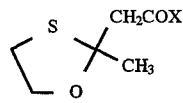

wherein X is as defined above,
in the presence of an effective amount of aqueous hydrogen peroxide and a sterically-hindered organoselenium compound of the formula

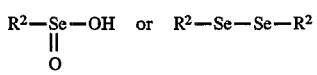

wherein R$^2$ is aryl, mono-, di- or tri-substituted with C$_1$–C$_3$ alkyl,
to the produce the 1,3-oxathiolane sulfoxide.

2. A process as recited in claim 1 wherein X is an amino group of the formula —NHR, wherein R is phenyl, nitrophenyl, (C$_1$–C$_4$ alkoxy)phenyl, halophenyl or hydroxyphenyl; or X is an alkoxy group of the formula —OR$^1$ wherein R$^1$ is C$_1$–C$_6$ alkyl.

3. A process as recited in claim 2 wherein X is an amino group of the formula —NHR, wherein R is phenyl.

4. A process as recited in claim 1 wherein the sterically-hindered organoselenium compound has the formula

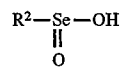

wherein R$^2$ is as defined in claim 1.

5. A process as recited in claim 4 wherein R$^2$ is phenyl, mono-, di- or tri-substituted with C$_1$–C$_3$ alkyl.

6. A process as recited in claim 5 wherein R$^2$ is phenyl, mono-, di- or tri-substituted with methyl.

7. A process as recited in claim 6 wherein R$^2$ is phenyl, tri-substituted with methyl.

8. A process as recited in claim 1 wherein the 1,3-oxathiolane sulfoxide is the cis stereoisomer of the 1,3-oxathiolane sulfoxide.

9. A process as recited in claim 8 wherein the cis stereoisomer of the 1,3-oxathiolane sulfoxide is substantially free of the trans stereoisomer of the 1,3-oxathiolane sulfoxide.

10. A process for the production of a 5,6-dihydro-2-methyl-1,4-oxathiin compound of the formula

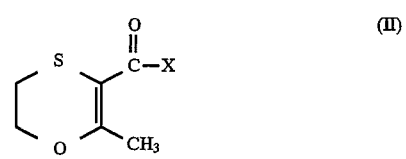

wherein X is an amino group of the formula —NHR, wherein R is hydrogen, phenyl, C$_1$–C$_8$ alkyl, C$_3$–C$_6$ cycloalkyl, nitrophenyl, (C$_1$–C$_4$ alkoxy)phenyl, furfuryl, halophenyl, tolyl, napthyl, biphenyl or hydroxyphenyl; or X is an alkoxy group of the formula —OR$^1$ wherein R' is C$_1$–C$_6$ alkyl,
which process comprises
(a) oxidizing a 1,3-oxathiolane of the formula

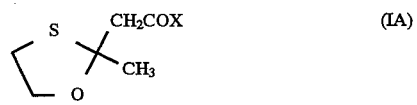

wherein X is as defined above,
in the presence of an effective amount of aqueous hydrogen peroxide and a sterically-hindered organoselenium compound of the formula

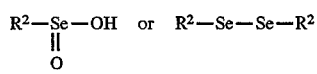

wherein R$^2$ is aryl, mono-, di- or tri-substituted with C$_1$–C$_3$ alkyl,
to the produce a 1,3-oxathiolane sulfoxide of the formula

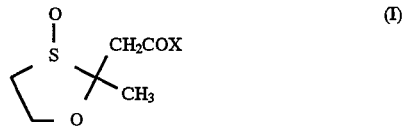

wherein X is as defined above; and
(b) combining the 1,3-oxathiolane sulfoxide with a non-protic organic solvent to form a reaction mixture; heating the reaction mixture at a temperature of about 30° C. to about 100° C., in the presence of an effective amount of an acid catalyst with a pK$_a$ of about 0.5 to about 4.5, while removing the water of reaction, to produce the 5,6-dihydro-2-methyl-1,4-oxathiin compound.

11. A process as recited in claim 10 wherein X is an amino group of the formula —NHR, wherein R is phenyl, nitrophenyl, ($C_1$-$C_4$ alkoxy)phenyl, halophenyl or hydroxyphenyl; or X is an alkoxy group of the formula —$OR^1$ wherein $R^1$ is $C_1$-$C_6$ alkyl.

12. A process as recited in claim 11 wherein X is an amino group of the formula —NHR, wherein R is phenyl.

13. A process as recited in claim 10 wherein the sterically-hindered organoselenium compound has the formula

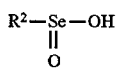

wherein $R^2$ is as defined in claim 10.

14. A process as recited in claim 13 wherein $R^2$ is phenyl, mono-, di- or tri-substituted with $C_1$-$C_3$ alkyl.

15. A process as recited in claim 14 wherein $R^2$ is phenyl, mono-, di- or tri-substituted with methyl.

16. A process as recited in claim 15 wherein $R^2$ is phenyl, tri-substituted with methyl.

17. A process as recited in claim 10 wherein the 1,3-oxathiolane sulfoxide is the cis stereoisomer of the 1,3-oxathiolane sulfoxide.

18. A process as recited in claim 17 wherein the cis stereoisomer of the 1,3-oxathiolane sulfoxide is substantially free of the trans stereoisomer of the 1,3-oxathiolane sulfoxide.

19. A process as recited in claim 10 wherein the nonprotic organic solvent is selected from the group consisting of an aromatic hydrocarbon having a boiling point not greater than 145° C., a chlorinated hydrocarbon having a boiling point not greater than 130° C., and an alkyl ester of an aliphatic acid having a boiling point not greater than 130° C.

20. A process as recited in claim 19 wherein the nonprotic organic solvent is selected from the group consisting of benzene, toluene, xylene, chloroform, dichloromethane, ethyl acetate, n-propyl acetate, and isopropyl acetate.

21. A process as recited in claim 19 wherein the nonprotic organic solvent is a chlorinated hydrocarbon having a boiling point not greater than 130° C.

22. A process as recited in claim 21 wherein the nonprotic organic solvent is dichloromethane.

* * * * *